United States Patent [19]

af Ekenstam et al.

[11] 4,282,986

[45] * Aug. 11, 1981

[54] METHOD FOR DISCHARGE OF QUANTITIES OF FLUID OR SEMI-FLUID SUBSTANCES FROM A CONTAINER

[75] Inventors: Bo T. af Ekenstam, Mölndal; Erik G. P. Nordqvist, Särö, both of Sweden

[73] Assignee: Landstingens Inkopscentral, Solna, Sweden

[*] Notice: The portion of the term of this patent subsequent to Feb. 7, 1995, has been disclaimed.

[21] Appl. No.: 861,843

[22] Filed: Dec. 19, 1977

Related U.S. Application Data

[63] Continuation-in-part of Ser. No. 661,177, Feb. 25, 1976, Pat. No. 4,072,249.

[30] Foreign Application Priority Data

Mar. 3, 1975 [SE] Sweden .................................. 7502318

[51] Int. Cl.³ .......................... B67B 7/00; B65D 37/00
[52] U.S. Cl. .......................................... 222/1; 222/81; 222/214; 222/215; 128/216
[58] Field of Search .................... 222/81, 107, 95, 214, 222/215, 1, 92, 212, 213, 210, 386.5; 206/820, 484; 128/232, 216 R

[56] References Cited

U.S. PATENT DOCUMENTS

| 798,093 | 8/1905 | Dean | 128/216 |
|---|---|---|---|
| 2,768,623 | 10/1956 | Marchand | 128/216 X |
| 3,145,879 | 8/1964 | Williams | 222/212 X |
| 3,473,524 | 10/1969 | Drewe | 222/215 X |
| 4,131,217 | 12/1978 | Sandegren | 128/216 X |

FOREIGN PATENT DOCUMENTS 790220  2/1958  United Kingdom ..................... 128/216

Primary Examiner—Allen N. Knowles
Attorney, Agent, or Firm—Hane, Roberts, Spiecens & Cohen

[57] ABSTRACT

A method of dispensing fluid or semi-fluid liquids or pastes in which the liquid or paste is contained in a container having a top flexible dome and a bottom dome connected at their open ends to each other. The method comprises pressing the top dome downwardly toward the bottom dome and forcing the top dome into the bottom dome and discharging the liquid or paste from the bottom dome under the action of the forcing of the top dome into the bottom dome. The top dome can be formed with an internal annular bead which is displaced along the inner walls of the bottom dome to scrape off material stuck to the inside walls of the bottom dome.

8 Claims, 42 Drawing Figures

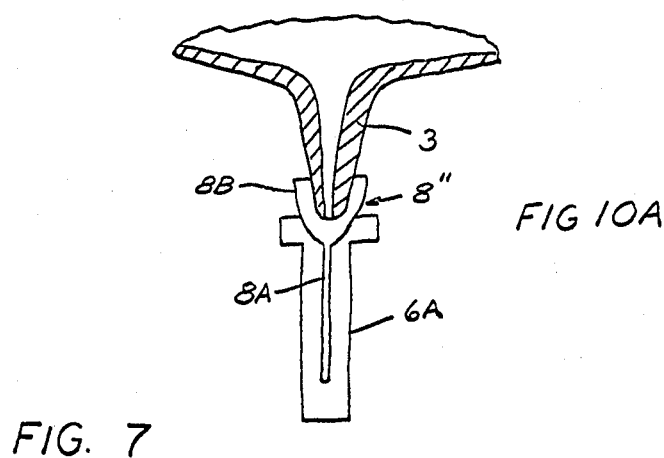
FIG. 7
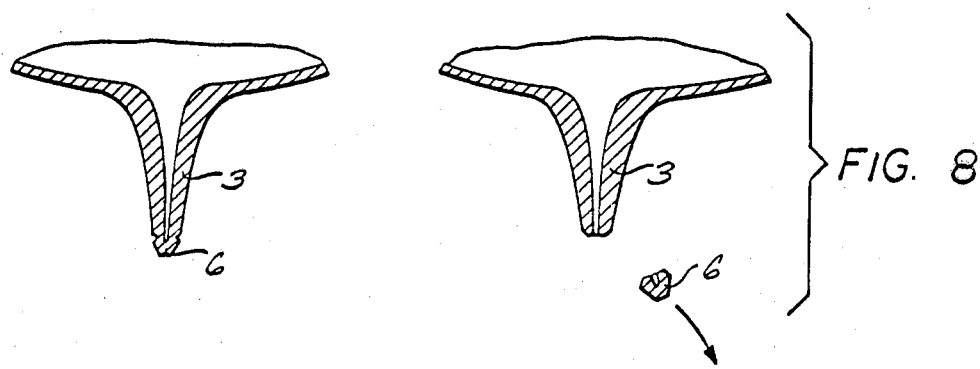
FIG. 8
FIG 10A
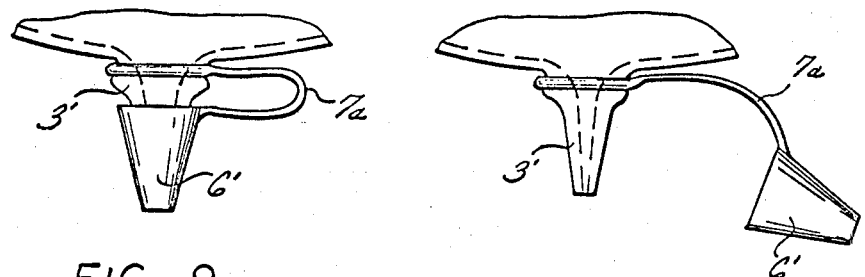
FIG. 9
FIG. 10

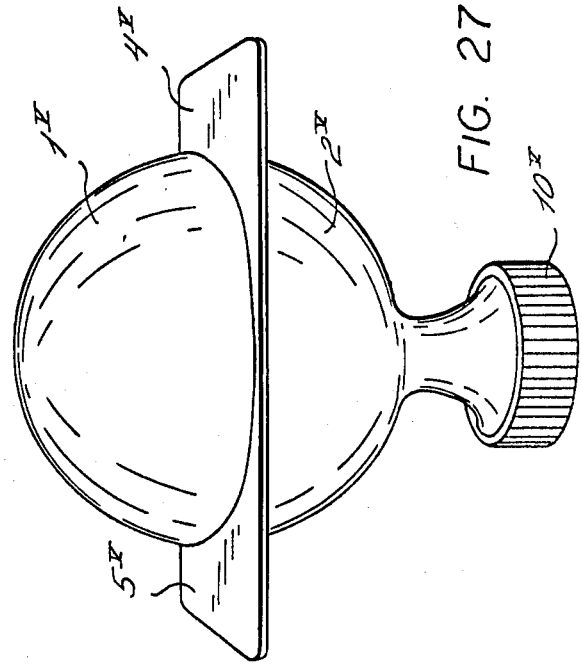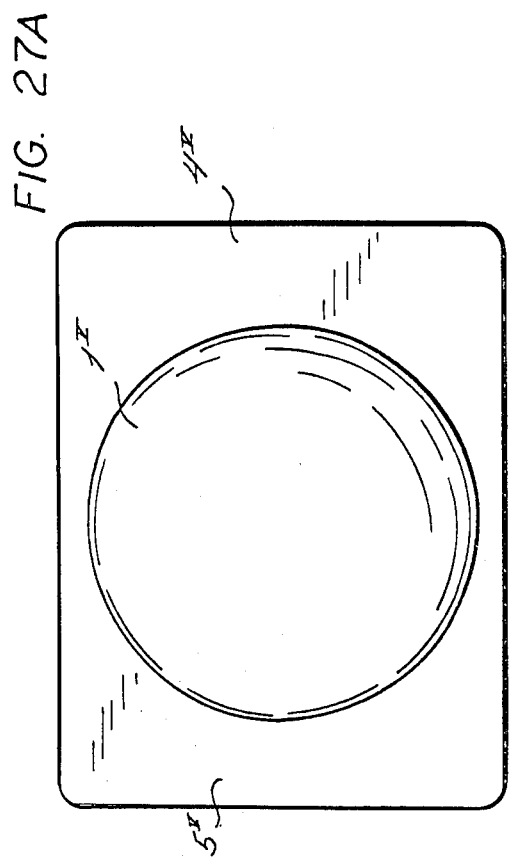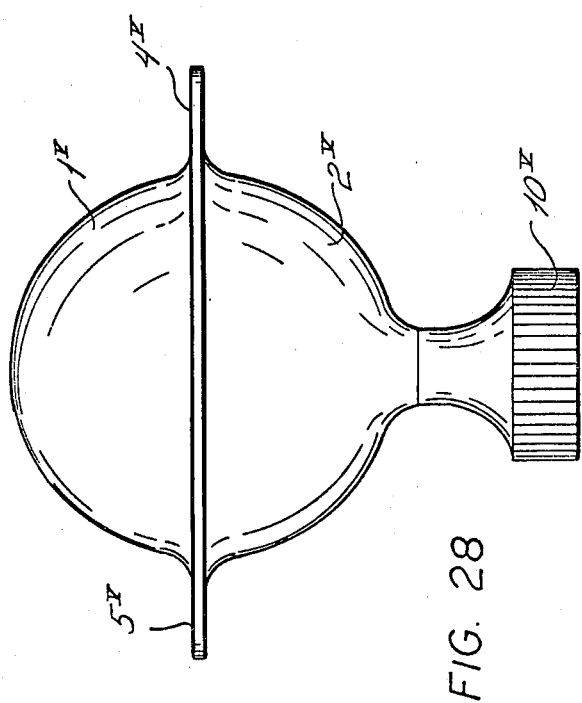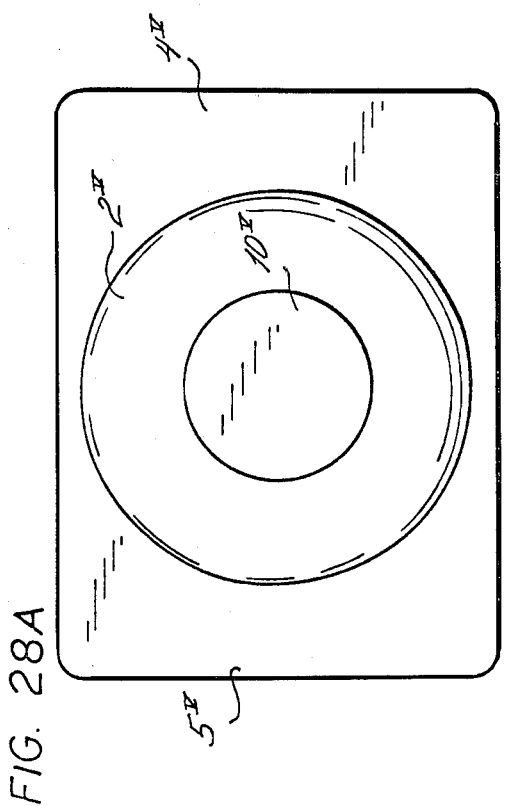

METHOD FOR DISCHARGE OF QUANTITIES OF FLUID OR SEMI-FLUID SUBSTANCES FROM A CONTAINER

CROSS-REFERENCE TO RELATED APPLICATION

This application is a continuation-in-part of Ser. No. 661,177 filed Feb. 25, 1976, now U.S. Pat. No. 4,072,249.

FIELD OF THE INVENTION

This invention relates to a container for fluid or semi-fluid substances in small quantities and to methods of discharging materials using such container. The substances to be packed according to the invention are mainly drugs; consequently the following description deals with such substances. However, it should be obvious that other substances can be packed in the described container.

PRIOR ART

In administering drugs, it is common to pack them in conventional tubes. The medical doctors Mone Hall, Percy Nordquist, Eva Palmgren and Irene Wilhelmsson have reported in a study at the National Medical Conference 1974 in Sweden that the conventional tube, irrespective of material used, is very difficult to handle, especially for older people. The test tubes used by the doctors have been of various types of existing tubes, containing substances having pharmacological effects. The study is considered to be highly representative for the kind of problems appearing in the use of tubes, and it is related in Svensk Läkartidning 1975 (Swedish Medical Journal).

Tubes are sometimes intended for one-time use and sometimes for repeated use. The tube always is such that by squeezing, a predetermined amount of the substance can be applied on a desired location of the patient. However, experience has shown that it is completely impossible to meet this requirement by using conventional tubes.

In the periodical Nord Emballage, Feb. 1975, Vol. 2, page 4, it is mentioned that it is possible to get more exact doses by using a specially designed valve. This is, of course, an improvement, but patients have difficulty in handling these tubes equipped with such valves. These kinds of tubes are also expensive, which is a serious disadvantage considering the large consumption of tubes in hospitals.

SUMMARY OF THE INVENTION

An object of this invention is to provide a container, which a patient, irrespective of age, can handle without difficulty.

According to the invention, the container can be placed between two fingers, and a thumb can be used to squeeze the contents out of the container. The container, according to the invention, has flanges such that it can be grasped by, for example, the index finger and the middle finger. Due to these flanges, it is also possible to manufacture an assembly of containers, where the containers are joined to each other by the flanges. In the joints between containers, there shall be indications of fracture, facilitating the separation of one container from the assembly and which can be used by the patient. By having the containers joined to each other, they form units which can easily fit into boxes. Packages containing several boxes can have such dimensions that a number of packages can form units of multiple packages. Subsequently, the handling of containers from factory to hospital becomes simpler.

A container according to this invention contains a top-part, a bottom-part, and protruding members forming the flanges that are gripped by the fingers when being squeezed. The bottom-part is normally made of rigid material and the top-part of flexible material. Both the top- and bottom-parts have a domed shape, preferably spherical or the like. Naturally, both parts can be made of flexible material, but then there must be arranged a rigid envelope having the protruding members thereon and which would envelope, to a lesser or greater degree, the bottom-part. According to the invention, it is appropriate for the top-part to be fitted with some type of a member for keeping a thumb securely in place. Such a member can be a friction lining or a particular shape of the upper part.

The top-part might also contain a member, as for example, a spring or other element of metal, arranged such that the position of the top-part remains after having been squeezed.

The container may also have permanent rib shaped deformations or the like, such that squeezing the top-part is made against a retaining force.

The top-part of the container might have a circular member arranged such that when the container is squeezed, this circular member scrapes substances sticking to the walls.

The bottom part of the container may have an opening which can be sealed with a cap. The bottom-part may have any kind of appropriate opening for emptying the container. The opening may be small or large and can be sealed by a cap having a locking device or threads.

The container according to the invention can also be fitted in a special device having a plunger such that the contents can be squeezed out by the plunger. This special device can also have means such that it can be gripped by the fingers and normally can take the place of the corresponding means of the container.

According to the invention, it is advantageous to make a number of bottom-parts forming one piece and then to fit the top-parts. The separate containers in such a unit can be filled with substance at the same time, for example, via the bottom-parts, and when using this method it is possible for the top-parts to be initially fully depressed into the bottom-part and that the substance used for filling is preheated.

BRIEF DESCRIPTION OF THE DRAWINGS

The invention is described in greater detail in connection with the accompanying drawings, wherein:

FIG. 7 shows a closed spout of a container, FIG. 8 shows an open spout, FIG. 9 shows another embodiment of a closed spout, FIG. 10 shows the spout of FIG. 9 after being opened, FIG. 10A shows a needle and cover assembly applied to the spout, FIG. 27 shows a perspective view of the same container as shown in FIG. 1 seen at an angle from the side, the grips for resting the fingers being rectangular so that a number of containers by joints between these grips can form a block, FIG. 27A is a top view of FIG. 27, FIG. 28 shows a side view of a container according to FIG. 27, FIG. 28A is a bottom view of FIG. 27.

DETAILED DESCRIPTION

Figure 1:
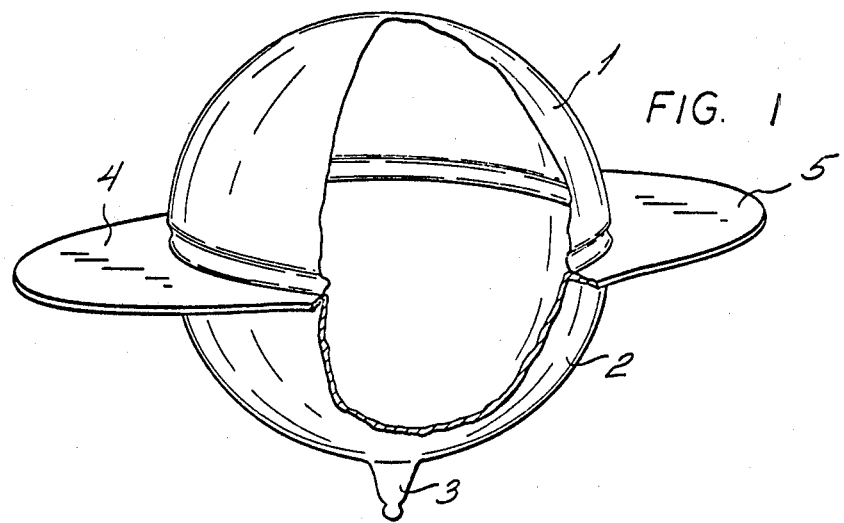
FIG. 1 shows an embodiment of a container according to the invention, either filled or ready to be filled with a substance.
Figure 3:
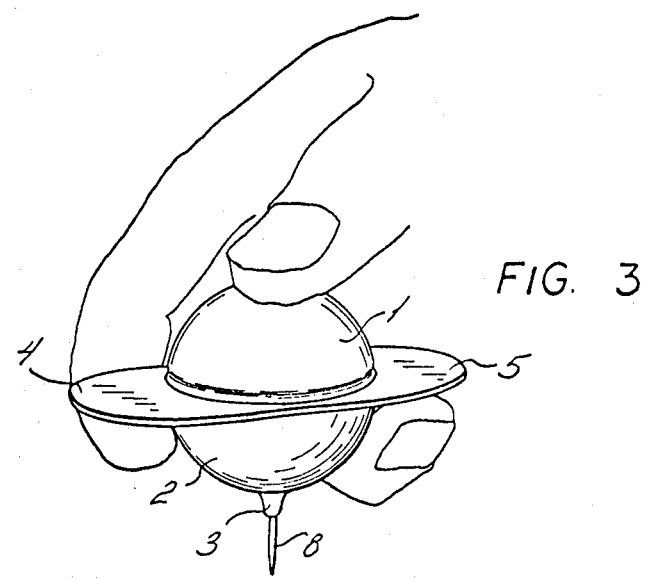
FIG. 3 shows a gripped container in the form of a one-time syringe and just before the squeezing takes place.
Figure 4:
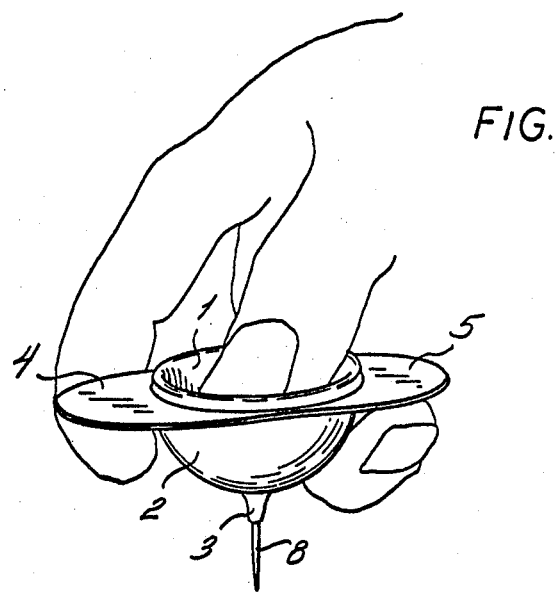
FIG. 4 shows the container of FIG. 3 after it is emptied.
Figure 5:
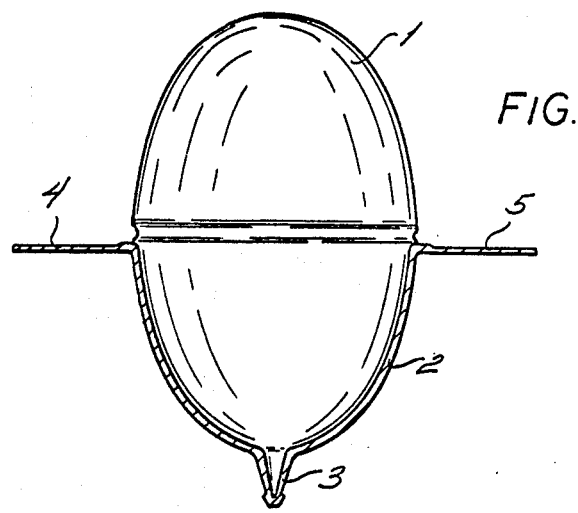
FIG. 5 shows a partial section of the container of FIG. 1.
Figure 6:
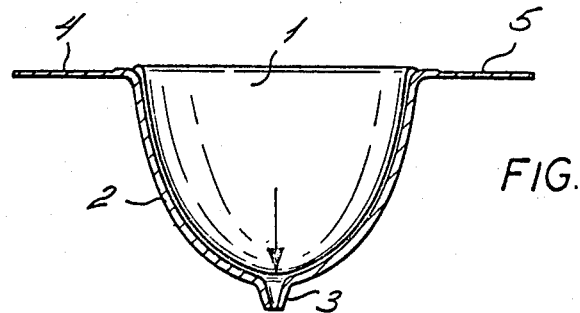
FIG. 6 shows a section of the container shown in FIG. 2.

In the drawing, reference numeral 1 refers to a dome-shaped part which is made of soft and ductile material. Numeral 2 refers also to a dome-shaped part, which is made of stiffer material and meant to retain its shape. The two dome-shaped parts are joined to each other at their openings as shown in FIG. 1, forming a container which is mainly spherical. However, it is obvious that the two joined parts can have any other shape. They could be, for example, cubical, rectangular or pyramidal; in other words the shape of the two joined parts can be varied in various ways. The two parts can, for example, be cylindrical and the free ends closed by hemispherical parts. It can be suitable to make a flat top on one of the dome-shaped parts, whereby the container can be placed on a table top or the like without rolling. The dome-shaped part 2 has a sealed spout 3 which can be opened when desired. At the joint between the two dome-shaped parts is an encircling lug which is elliptical such that the two lips or flanges 4 and 5 are formed. Naturally, the lug can be given any suitable shape. It is suitable to minimize the size of the dome-shaped parts in order to facilitate the use of the container as shown in FIGS. 3 and 4. To the spout 3 any suitable means can be connected for applying the substance leaving the spout. Consequently, a hypodermic needle can be connected to the container, when it contains a liquid substance. A flexible or stiff tube could be connected to the container.

In FIGS. 7 and 8 there is shown a spout 3, which has a sealing 6, which together with the spout forms a single unit. This type of sealing can be cut off as shown in FIG. 8.

FIG. 9 shows a spout 3', which is sealed by a cap 6', which is tied by a link 7a to the spout 3', alternatively, the cap could be tied by the link to the container. FIG. 9 shows the spout 3' sealed by the cap and FIG. 10 when the cap is removed.

Figure 2:
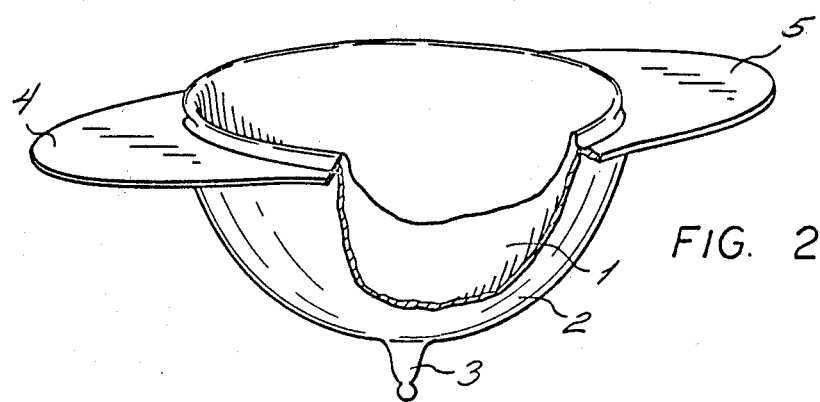
FIG. 2 shows the same container as in FIG. 1 but emptied.

The container according to the invention is such that the dome-shaped part 1 can, by squeezing or the like, take the shape shown in FIG. 2; in other words the wall of the dome-shaped part 1 is flexible so that it can adjust to a lesser or greater extent, to the inside of the dome-shaped part 2. Any materials can be used which fulfill the function shown in FIGS. 1 and 2. A suitable material both for parts 1 and 2 would be a plastic, where the plastic in part 1 is flexible and that in part 2 be rather stiff. Naturally it is also possible for part 2 to be made of metal and part 1 of metal foil. Combinations such as stiff and thin cardboard or glass and rubber are also possible.

It is practicable to construct the wall of part 1 in such a way that when the container has been squeezed, the wall remains as is just before the squeezing is completed. To this end, elements, such as for example, ribs of suitable material could be molded as integral parts of part 1. It is also possible to include additional elements such that the dome-shaped part 1 has a tendency to instantly switch over to the position shown in FIG. 2, when triggered by pressure on top of part 1.

The container as described is, for example, used in the following way. The user opens the spout 3', eventually he connects something thereto, for example, a tube or a hypodermic needle; and then he squeezes the container as shown in FIG. 3. In FIGS. 3 and 4, the container is fitted with a hypodermic needle 8. Holding the container as shown in FIG. 3, the needle is inserted in the part of the body to receive the injection. Now the user uses his thumb to press the top of the dome-shaped part 1 as shown in FIG. 4, the pressure being applied until part 1 is in the position shown in FIGS. 2 and 4, whereby the container is emptied. The flanges 4 and 5 serve as a gripping means for applying counter-pressure to the dispenser as shown in FIGS. 3 and 4. As seen in these figures, the counter pressure of the fingers on flanges 4 and 5 acts outside the periphery of the dome-shaped parts 1 and 2 thereby affording stability for the dispenser; also the action of the counterpressure at the level of the connection of the dome-shaped portions keeps the fingers of the user away from hypodermic needle 8 as seen in FIGS. 3 and 4; additionally, it is evident from FIGS. 3 and 4 that the presence of the flanges 4 and 5 insure that pressure application by the thumb will be limited to dome-shaped part 1.

FIG. 10A shows a hypodermic needle and cover assembly applied to the opened spout 3. Namely, as seen in FIG. 10A, the spout 3 has a removable hypodermic needle unit 8" sealably pressed thereon, and a cover 6A removably engaged on needle unit 8". In use, the cover 6A is removed from the needle unit and the container is emptied in the manner shown in FIG. 3. The assembly of needle unit 8" and cover 6A can be furnished in a sealed, sterile package which is opened to gain access to the assembly. Then the assembly is mounted on the opened spout and the cover 6A is removed. The needle unit 8" comprises a hypodermic needle 8A and a cuff portion 8B of flexible material, such as rubber or plastic, which can be tightly engaged on the spout.

Figure 11:
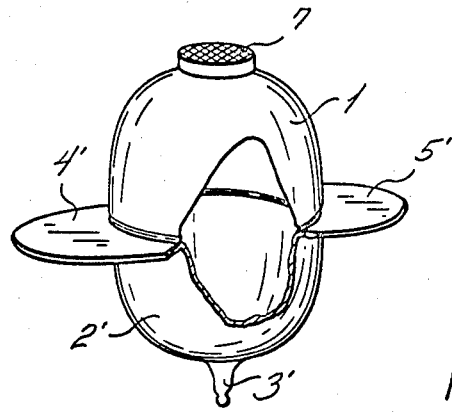
FIG. 11 shows a perspective view of a container similar to the container in FIG. 1, however, having a more cylindrical shape and fitted with a grip for a squeezing finger.

FIG. 11 shows a container similar to that described above where both dome-shaped parts are indicated respectively at 1' and 2'. They differ from the dome-shaped parts shown above in that they are cylindrical and one end of each part forms a hemisphere. The dome-shaped part 1' has on its top a protuberance 7 suitably shaped to be pressed by a finger. The protuberance can of course have a smooth surface, but it is preferred that the surface have such properties that a finger of the user will not slip when pressing the container.

Figure 12:
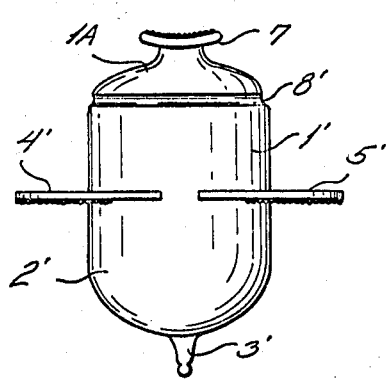
FIG. 12 shows partly in section a container similar to the container in FIG. 11 but modified such that it has a dished circular bead, designed to act as a member for scraping substances as may be sticking to the walls when emptying the container.
Figure 13:
Figure 12A:
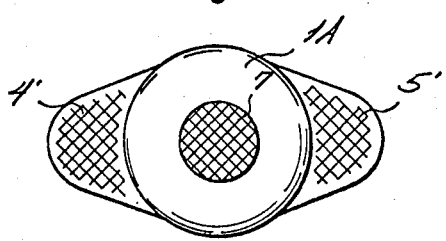
FIG. 12A is a top view of FIG. 12, FIGS. 13 and 14 show details of the container of FIG. 12 in two different operational stages.
Figure 14:
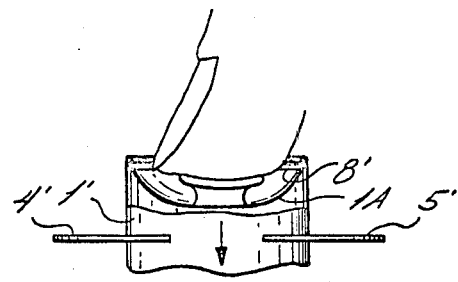

The container in FIG. 12 differs from that in FIG. 11 in that the dome-shaped part 1' has a recessed circular bead 8' preferably situated where the cylindrical shape turns into the hemispherical shape. The hemispherical part of the dome-shaped part 1' is indicated by numeral 1A. The circular bead 8' is designed to act as a member for scraping the substance sticking to the walls when emptying the container. This is especially shown in FIG. 14, when part 1A is pressed down. It shows how the circular bead 8' fits into the cylindrical part of the container.

Figure 16:
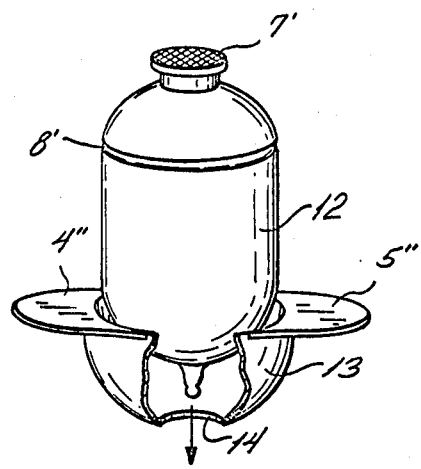
FIG. 16 shows a perspective view, partly in section, of a container similar to the container of FIG. 12, where both the top-part and the bottom-part are made of flexible material and where the bottom-part is partly enclosed by an envelope of hard material.

FIG. 16 shows a container made in one piece which is indicated by numeral 12. The shape of the container is similar to the container according to FIG. 11. The container 12 is made of flexible material and in order to have necessary rigidity, the end with the spout has an envelope 13 of hard material. The envelope has two flanges 4" and 5" for the fingers, similar to the flanges 4' and 5'. The envelope also has an opening 14 for the spout. The container has a circular bead 8' as described in connection with FIG. 11 and also a protuberance 7'.

Figure 17:
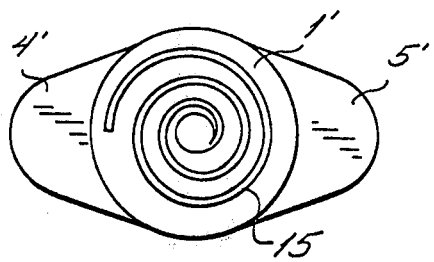
FIGS. 17 and 18 show modifications of the top part of a container and more particularly elements for pressing down the top-part toward the bottom-part.

FIG. 17 shows how the top-part 1' can have an integrally moulded spiral 15, the objective of which is to distribute the applied pressure to a greater area of the top of part 1' when emptying the container.

Figure 18:
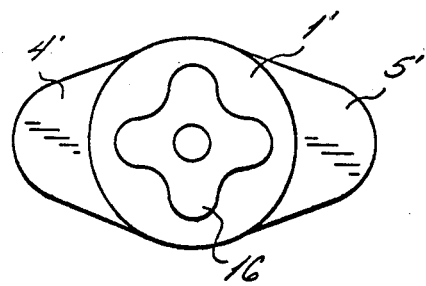

FIG. 18 shows another integrally molded element 16 having the same function as the spiral in FIG. 17.

The two elements in FIGS. 17 and 18 can be made of any material as long as they function as desired.

Figure 19:
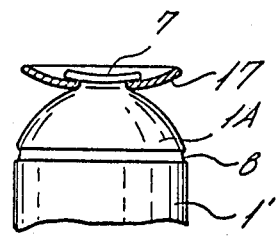
FIG. 19 shows a member on the outside of the top-part of a container, said member acting as a locking device for holding the top-part in position when pressed on by a finger.

FIG. 19 shows the top-part of a container according to FIG. 12 fitted with a disc 17 shaped somewhat like a plate and with its outer edge pointing out from the container. In the center, the disc has a hole matching and fixed to the protuberance 7 on the part 1A. The disc can be made of any suitable material, for example, plastic or metal and it may be resilient. The purpose of the disc 17 is to act as a catching device inside the cylinder being formed when part 1' is pushed. When pressure on the protuberance 7 ceases the disc 17 prevent the part 1' from springing back. How the cylinder is deformed is, for example, shown in FIG. 14.

The containers according to FIG. 1 or to FIG. 11 naturally can be used in a device containing a plunger replacing a human thumb.

Figure 20:
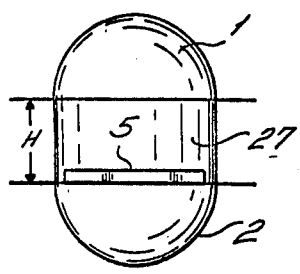
FIG. 20 shows an elevational view of a container similar to FIG. 1 but of cylindrical configuration.
Figure 20A:
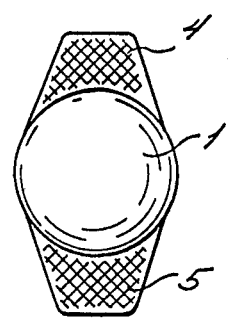
FIG. 20A is a top view of FIG. 20.

FIG. 20 shows a container having a central part 27 of a length H, which central part preferably has a non-circular cross section. However, a container can be made having a cylindrical central part with hemispheres as top-part 1 and bottom-part 2. (See FIG. 11.) This embodiment, having the length H greater than zero, is referred to as a cylgloboid and embodiment 1. If the length H is equal to zero, the container becomes the same as shown in FIG. 1.

Figure 21:
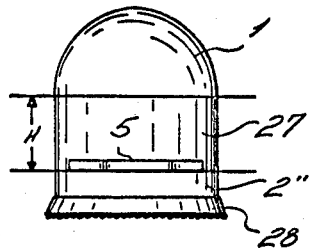
FIG. 21 shows a cylglobid shape container having a flat bottom.
Figure 21A:
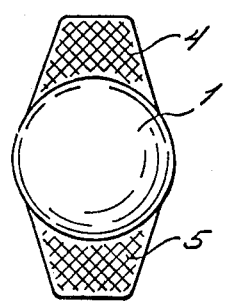
FIG. 21A is a bottom view of FIG. 21.

FIG. 21 shows the same container as in FIG. 20 but where the bottom-part 2" has a large opening covered by a lid 28.

Figure 22A:
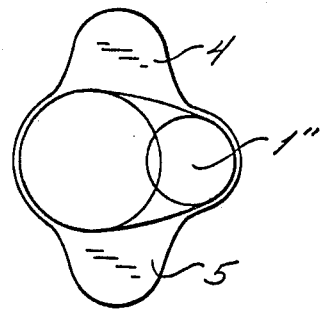
FIG. 22A is a top view of FIG. 22.
Figure 22:
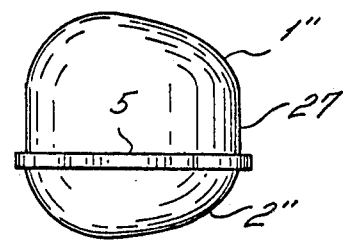
FIG. 22 shows a side view of a cylovid shaped container.
Figure 23A:
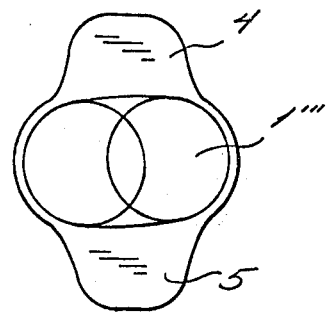
FIG. 23A is a top view of FIG. 23.
Figure 23:
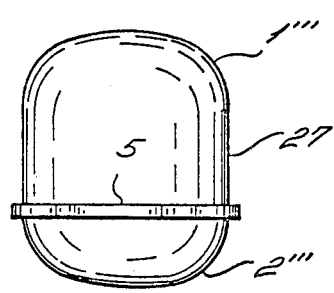
FIG. 23 shows a side view of a container having a cyleliden shape.

The embodiments according to the FIGS. 22 and 23 are given shapes which are optimal with regard to adaptations to fingers, when using the thumb together with the index finger and the middle finger for emptying the container.

In FIG. 22, the top-part 1" is adopted to the shape of the thumb. The fingerprint of the thumb in combination with the cross-section of the tip of the thumb forms a volume similar to half an egg cut from tip to tip. When the container is made with a central part 27 and a top-part and a bottom-part shaped like said volume, it will be easy using the thumb, the index and the middle fingers to press the top-part 1" through the central part 28 down to the corresponding bottom-part 2". The spout is preferably positioned in the lowest area of the bottom-part. If the container is made without a central part, which is the same as H=zero, it takes the shape of an egg. The embodiment having the length H greater then zero, as shown in the Figure, is known as a cylovid.

FIG. 23 shows a container having a top-part 1'" and a bottom-part 2'" each part being shaped as a semi-ellipsoid cut along the largest diameter. When such top- and bottom-parts are joined with a central part 27, an embodiment is formed called a cylelid. If the length H of the central part is equal to zero, the shape of the container will be an ellipsoid.

Common for all the embodiments according to the FIGS. 20–23 is that when H is greater than zero, the top- and bottom-parts are separated by an envelope surface forming the central part, which envelope surface is theoretically formed when a generatrix is moved perpendicular to and along all of the envelope of the maximum cross section of an end part.

Figure 24:
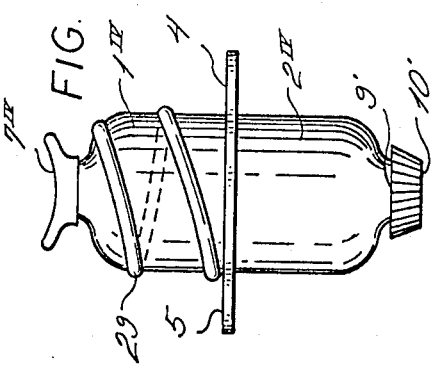
FIG. 24 shows a container similar to the one shown in FIG. 11 but with a top-part having a spiral-shaped bead acting as a spring.
Figure 24A:
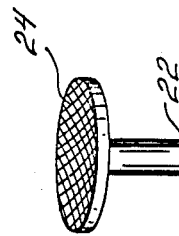
FIG. 24A is a top view of FIG. 24.
Figure 24B:
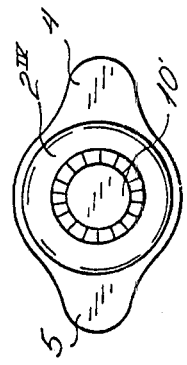
FIG. 24B is a bottom view of FIG. 24.

FIG. 24 shows a container corresponding to the one shown in FIG. 11. On the top-part $1^{IV}$ is arranged a spiral-shaped bead 29. The container has, like the ones previously described, a part $7^{IV}$ for a thumb and two flanges 4 and 5, for gripping by the forefinger and the middle finger when used, and additionally a bottom-part $2^{IV}$. The bottom-part has an opening 9' which can be sealed with a cap 10'. The spiral-shaped bead 29 gives resistance to the pressure from a thumb, facilitating conditions for a smooth and controlled application of the substance stored in the container.

Figure 25:
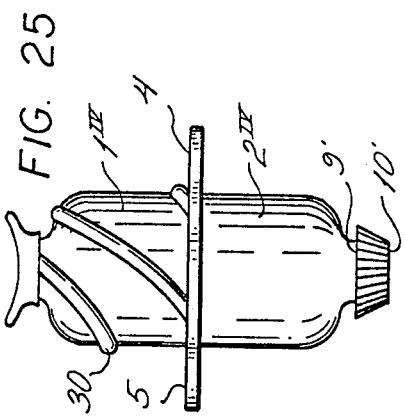
FIG. 25 shows the same container as in FIG. 24 but with a different spiral head.
Figure 25A:
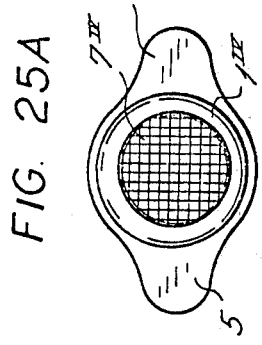
FIG. 25A is a top view of FIG. 25.
Figure 25B:
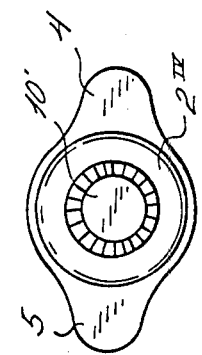
FIG. 25B is a bottom view of FIG. 25.

FIG. 25 shows a container having exactly the same properties as the container in FIG. 24, but where the single bead is modified such that the top-part has a number of beads as shown.

Figure 26:
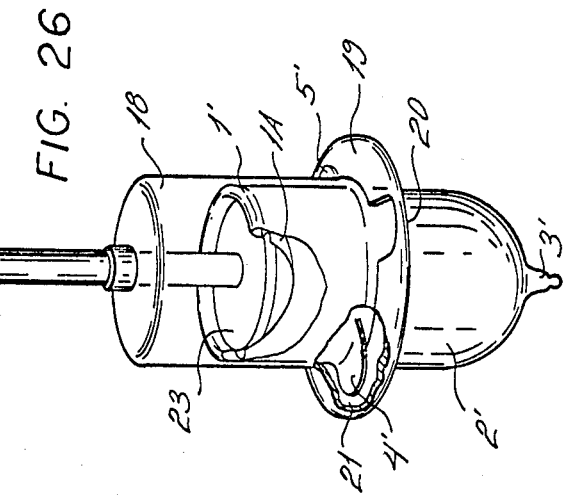
FIG. 26 shows a perspective view of a squeezing device for a container according to one or several of shown embodiments.

FIG. 26 shows another device for emptying a container according to the invention. The device has a cylindrical cap 18, which at its open end has a circular pocket 21 formed by a double-folded corbelled rim 19 and 20. The circular pocket 21 is intended to surround the flanges 4' and 5' of a container 1', 2'. The cap 18 is fitted with a plunger 22 which has a press plate 23 and a finger part 24. For emptying a container according to this invention using a device as described, the unit is placed between two fingers in such a way that part 20 of the rim is gripped by said fingers. The thumb is put on the fingerpart 24, and by pressing the plunger 22, the container 1', 2' is emptied.

Figure 15:
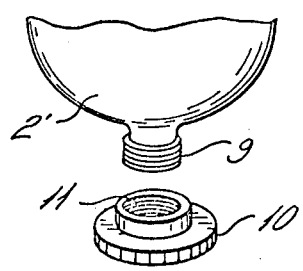
FIG. 15 shows an exploded view of the bottom part of a container having an opening with a screw cap.

The spout 3 can be made cylindrical and provided with threads 9 as shown in FIG. 15. A cap 10 can be mounted on the spout by corresponding threads 11.

Again, it should be noted that all the flanges of the container adapted to the fingers are made so that the emptying is done smoothly and controllably. This implies that the design has to be based on an empirical study of the fingers and their physiological coordination. Embodiments and sizes of said containers should be designed taking a number of parameters into consideration, such as for example, length, angle, surface and size of finger tips, finger joints, and all the fingers in order to have optimal effects and as few types as possible.

Figure 29:
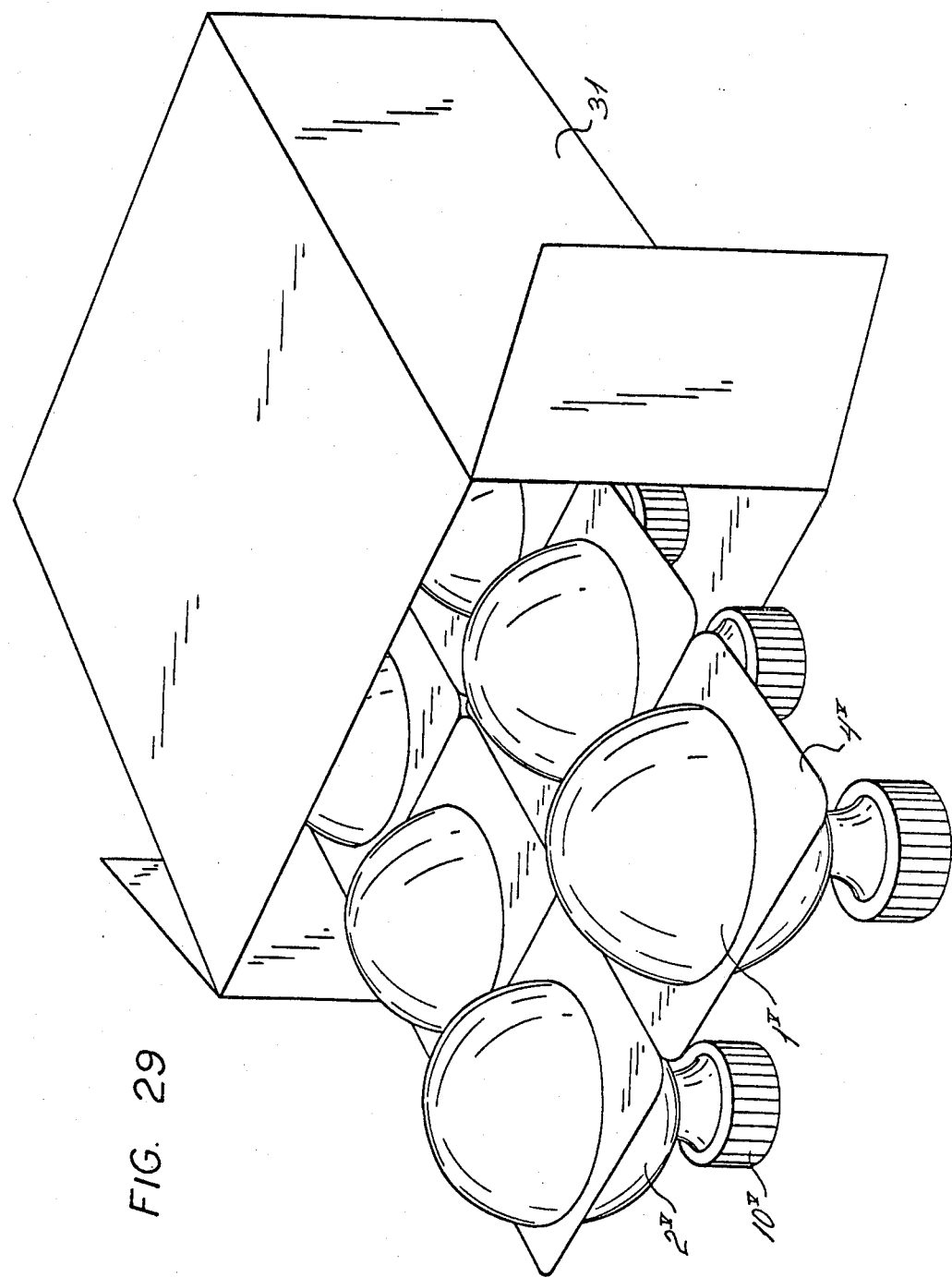
FIG. 29 shows a number of containers forming a block which can be slid into a box.
Figure 30:
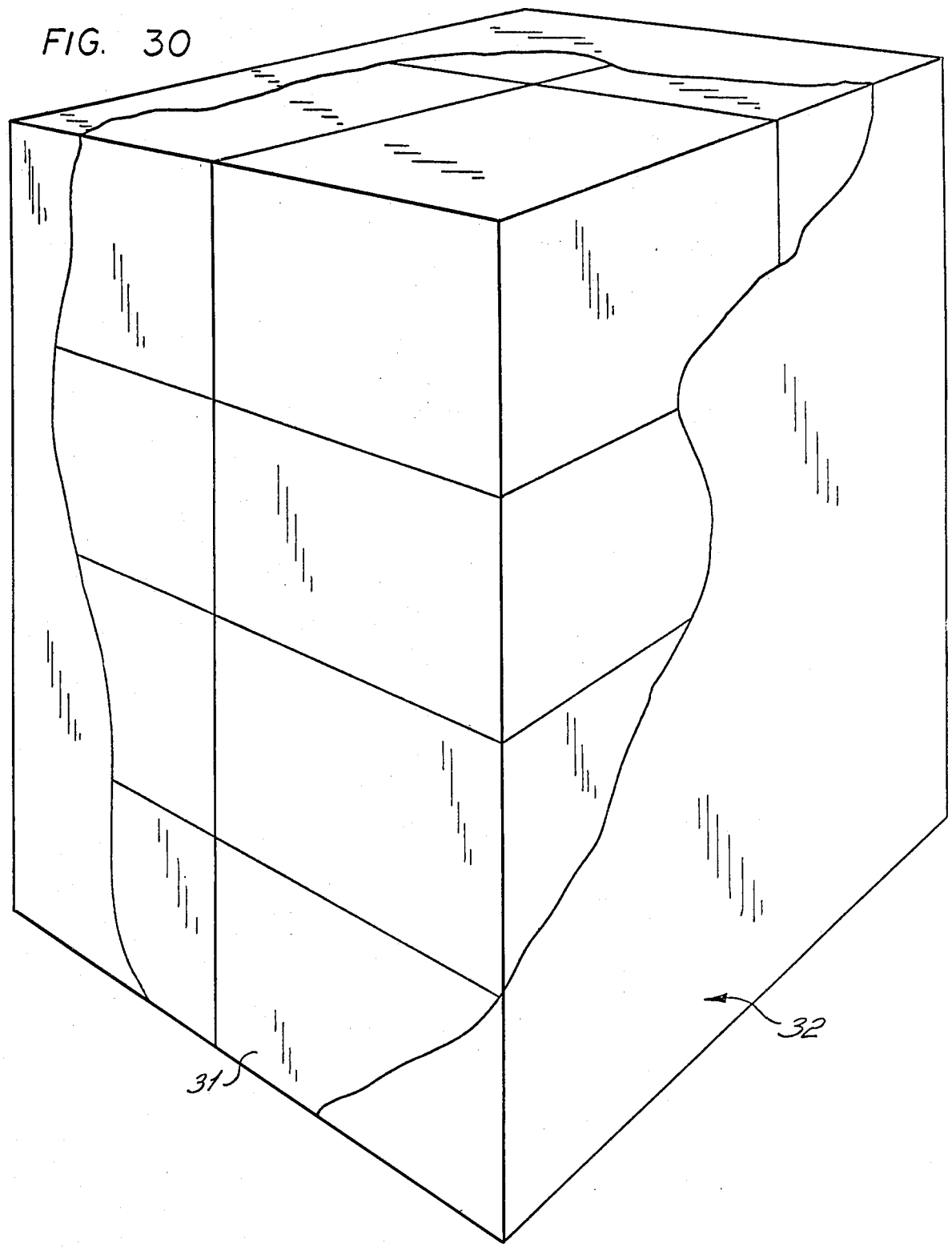
FIG. 30 shows a unit containing a number of the boxes shown in FIG. 29.

FIGS. 27 and 28 show a container having a top-part $1^V$ and a bottom-part $2^V$. The container has two flanges $4^V$ and $5^V$ together forming a rectangular surface. The bottom-part $2^V$ has an opening with a sealing member $10^V$ which is cylindrical and prevents the container from staying upright on a horizontal surface. Because of the rectangular shape of the flanges, a number of containers can be joined to each other, forming an assembly as shown in FIG. 29. Between the flanges are indications of fracture making it possible to break off one container at a time from the block. By making assemblies of containers, these assemblies can conveniently be packed in boxes 31 which can form multiple packages enclosed in wrapping 32, such as, for example, thermoplastic foil.

When manufacturing the assemblies according to FIG. 29, the bottom-parts together with the flanges can be made in one step in one tool, after which this part is fitted with the top-parts, separately made or equally made as one unit.

What is claimed is:

1. A method of dispensing fluid or semi-fluid liquids or pastes in which said liquid or paste is contained in a container having a top flexible dome and a bottom dome connected at their open ends to each other and a laterally projecting gripping means at the connection of the open ends of the domes, the bottom dome having a closed spout remote from the open end thereof, said method comprising: forming an opening in said spout, affixing a hypodermic needle to said spout at said opening, pressing said top dome downwardly toward said bottom dome and forcing said top dome into said bottom dome while applying counter-pressure to the gripping means, and discharging said liquid or paste from said bottom dome through the open spout and hypodermic needle under the action of the forcing of the top dome into the bottom dome and the application of the counter-pressure to the gripping means, said counter-pressure acting outside the periphery of the domes whereby to provide stability while also acting at the level of the connection of the domes whereby the fingers of the user are remote from the hypodermic needle, the gripping means also serving to limit the pressing action to the top dome.

2. The method according to claim 1 wherein the needle is removably affixed to the spout.

3. The method according to claim 1 comprising temporarily covering the needle prior to discharge of the material.

4. A method of dispensing fluid or semi-fluid liquids or pastes in which said liquid or paste is contained in a container having a top flexible dome and a bottom come connected at their open ends to each other and a laterally projecting gripping means at a connection of the open ends of the domes, the bottom dome having a closed spout remote from the open end thereof, said method comprising forming an opening in said spout, removably affixing a hypodermic needle to the spout at said opening, forming a cuff on the hypodermic needle for tightly engaging the spout, pressing said top dome downwardly toward said bottom dome and forcing said top dome into said bottom dome while applying counter-pressure to the gripping means, and discharging said liquid or paste from said bottom dome through the open spout and hypodermic needle under the action of the forcing of the top dome into the bottom dome and the application of the counter-pressure to the gripping means, said counter-pressure acting outside the periphery of the domes whereby to provide stability while also acting at the level of the connection of the domes whereby the fingers of the user are remote from the hypodermic needle, the gripping means also serving to limit the pressing action to the top dome.

5. A method of dispensing fluid or semi-fluid liquids or pastes in which said liquid or paste is contained in a container having a top flexible dome and a bottom dome connected at their open ends to each other, said method comprising: pressing said top dome downwardly toward said bottom dome and forcing said top dome into said bottom dome, and discharging said liquid or paste from said bottom dome under the action of the forcing of the top dome into the bottom dome, said step of pressing said top dome comprising scraping off material stuck to the inside walls of said bottom dome for discharge of said material.

6. The method according to claim 5 wherein said step of pressing further comprises gripping flanges mounted about the connected open ends of said top and bottom domes with two fingers, and pressing downwardly on the top of said top dome with a thumb.

7. A method of dispensing fluid or semi-fluid liquids or pastes in which said liquid or paste is contained in a container having a top flexible dome and a bottom dome connected at their open ends to each other, said method comprising: pressing said top dome downwardly toward said bottom dome and forcing said top dome into said bottom dome, and discharging said liquid or paste from said bottom dome under the action of the forcing of the top dome into the bottom dome, said top dome being formed with an internal annular bead which is displaced along the inner walls of the bottom dome to scrape material therefrom as the top dome is pressed into the bottom dome.

8. The method according to claim 7 wherein said top dome is deformed inwardly when pressure is applied thereto.

* * * * *